United States Patent
Peeters

(10) Patent No.: US 11,369,557 B2
(45) Date of Patent: Jun. 28, 2022

(54) CONCENTRATE COMPRISING AT LEAST ONE MANNOSYLERYTHRITOL LIPID AND AT LEAST ONE POLYGLYCEROL AND FATTY ACID ESTER

(71) Applicant: OLEON NV, Evergem (BE)

(72) Inventor: Hilde Peeters, Keerbergen (BE)

(73) Assignee: OLEON NV, Evergem (BE)

( * ) Notice: Subject to any disclaimer, the term of this patent is extended or adjusted under 35 U.S.C. 154(b) by 0 days.

(21) Appl. No.: 16/494,750

(22) PCT Filed: Mar. 16, 2018

(86) PCT No.: PCT/EP2018/056710
§ 371 (c)(1),
(2) Date: Sep. 16, 2019

(87) PCT Pub. No.: WO2018/167285
PCT Pub. Date: Sep. 20, 2018

(65) Prior Publication Data
US 2020/0093725 A1    Mar. 26, 2020

(51) Int. Cl.
*A61K 8/60* (2006.01)
*A61K 8/04* (2006.01)
*A61K 8/37* (2006.01)
*A61Q 1/14* (2006.01)

(52) U.S. Cl.
CPC ............ *A61K 8/60* (2013.01); *A61K 8/042* (2013.01); *A61K 8/375* (2013.01); *A61Q 1/14* (2013.01); *A61K 2800/48* (2013.01)

(58) Field of Classification Search
CPC .......... A61K 8/60; A61K 8/042; A61K 8/375; A61K 2800/48; A61Q 1/14
See application file for complete search history.

(56) References Cited

U.S. PATENT DOCUMENTS

| | | | |
|---|---|---|---|
| 2017/0071835 A1* | 3/2017 | Schelges | A61K 8/365 |
| 2017/0071837 A1 | 3/2017 | Schelges et al. | |
| 2018/0280261 A1* | 10/2018 | Nioh | A61K 8/64 |

FOREIGN PATENT DOCUMENTS

| | | | | |
|---|---|---|---|---|
| EP | 0579159 B1 | * | 1/1998 | A61Q 19/00 |
| EP | 2468842 B1 | * | 12/2016 | A61K 8/368 |
| EP | 3115355 A1 | | 1/2017 | |
| JP | 2011168548 A | | 9/2011 | |
| WO | WO-2017158194 A1 | * | 9/2017 | A61K 8/602 |

OTHER PUBLICATIONS

Schott. Comments on Hydrophile-Lipophile Balance Systems. J. Pharm. Sciences, 1990, 79(1):86-88. (Year: 1990).*
International Search Report received in PCT/EP2018/056710 dated May 7, 2018 with English Translation.
Mintel, "Vino Moisturizing Face Mask", http://www.gnpd.com, Mar. 2014.
Fukuoka et al., "Enzymatic Synthesis of a Novel Glycolipid Biosurfactant, Mannosylerythritol Lipid-D and its Aqueous Phase Behavior," Carbohydrate Research, vol. 346, 2011, pp. 266-271.
Rau et al., "Downstream Processing of Mannosylerythritol Lipids Produced by Pseudoyma Aphidis," Eur. J. Lipid Sci. Technol., vol. 107, 2005, pp. 373-380.

* cited by examiner

*Primary Examiner* — Robert A Wax
*Assistant Examiner* — Olga V. Tcherkasskaya
(74) *Attorney, Agent, or Firm* — Arentfox Schiff LLP

(57) ABSTRACT

The invention relates to a concentrate comprising at least one mannosylerythritol lipid and at least one polyglycerol and fatty acid ester, to a method for the production thereof, and to the uses of same, particularly as a thickening, foaming and/or cleaning agent.

12 Claims, 1 Drawing Sheet

Figure 1:
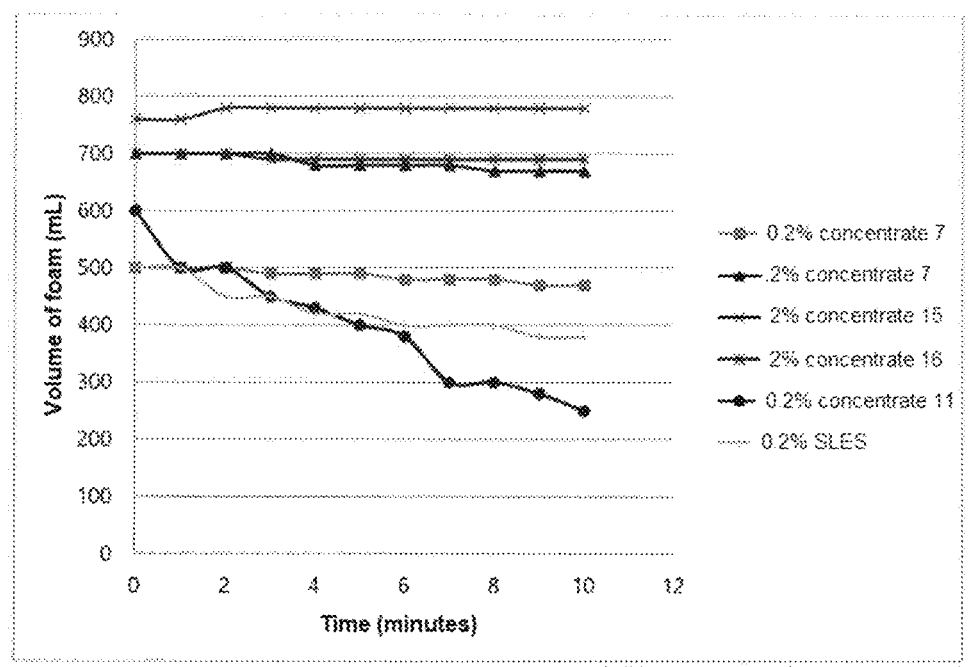

CONCENTRATE COMPRISING AT LEAST ONE MANNOSYLERYTHRITOL LIPID AND AT LEAST ONE POLYGLYCEROL AND FATTY ACID ESTER

CROSS-REFERENCE TO RELATED APPLICATIONS

This application is a National Stage Entry of PCT/EP2018/056710, filed Mar. 16, 2018, which claims priority to French Patent Application No. 1752241 filed on Mar. 17, 2017, the disclosure of which are hereby incorporated by reference in its entirety.

The present invention relates to a concentrate and to compositions comprising same. The present invention also relates to a process for the preparation of the concentrate and of the compositions according to the invention and uses thereof, in particular use of the concentrate according to the invention as a thickening, foaming and/or cleaning (detergent) agent.

Thickening, foaming and/or cleaning agents are used in many fields. It is known in particular to use thickening, foaming and/or cleaning agents in cosmetics, for example in makeup removal compositions. It is also known to use thickening, foaming and/or cleaning agents in the cleaning industry, for example in the preparation of cleaning or detergent products such as household or industrial maintenance compositions, in particular compositions for cleaning hard surfaces, or dishwashing products.

Cocamide diethanolamine (or cocamide DEA) is a surfactant having good foaming and thickening properties, usually used in cleaning compositions such as dishwashing products, or in cosmetics. It is also common to use sulphated compounds, such as sodium lauryl sulphate (SLS) or sodium lauryl ether sulphate (SLES). These sulphated surfactants have very good foaming and cleaning properties. Cocamide DEA and the sulphated compounds can be used in combination, so as to combine the foaming, thickening and cleaning properties of these compounds.

However, cocamide DEA and the sulphated compounds such as SLS and SLES are regarded as substances that are hazardous to human health.

In particular, cocamide DEA is thought to be a potential carcinogen.

As regards SLS and SLES, they are irritants to the skin and eyes. Furthermore, these compounds are corrosive, and would thus cause the deterioration of the lipids and fats of which the muscles and skin are composed. Moreover, SLS and SLES are generally contaminated with a carcinogen, 1,4-dioxane, which is a by-product of the manufacturing process of these sulphated compounds.

Therefore there is currently a need for solutions to replace these hazardous substances.

More particularly, it would be beneficial to develop agents:
  having a good surface-active property,
  having at the same time good thickening, foaming and/or cleaning properties,
  allowing stable foams to be obtained, and
  that would be less toxic to users.

The work of the inventor has made it possible to demonstrate that a specific concentrate had all of the above-described advantageous properties.

The invention thus relates to a concentrate comprising:
  at least 20% by weight of at least one mannosylerythritol lipid, with respect to the total weight of the concentrate, and
  at least 30% by weight of at least one polyglycerol fatty acid ester, with respect to the total weight of the concentrate,
  in which the ratio of mannosylerythritol lipid(s)/polyglycerol fatty acid ester(s) is comprised within the range [1/3; 3/1].

It will be noted that within the framework of the present application, unless otherwise stated, by "ratio" is meant the ratio by weight and the ranges of values indicated are understood inclusive of boundaries.

By "mannosylerythritol lipid" or MEL is meant a surfactant comprising a hydrophilic part formed by the mannosylerythritol group, and a hydrophobic part formed by at least one acyl group.

By MEL is meant more particularly a molecule having the following general formula (I):

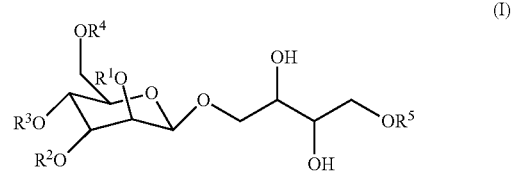

(I)

in which:
  $R^1$ and $R^2$, identical or different, represent an acyl group, comprising an unsaturated or saturated, acyclic carbon-containing chain,
  $R^3$ and $R^4$, identical or different, represent an acetyl group or a hydrogen atom, and
  $R^5$ represents a hydrogen atom or an acyl group.

Among the MELs of formula (I) described above, the "di-acylated MELs" and "tri-acylated MELs" can be distinguished according to the nature of the group present in position $R^5$. It will be noted that according to this terminology, the acetyl groups capable of being present in positions $R^3$ and $R^4$ are not accounted for in the acyl groups.

By "tri-acylated MEL" is meant a molecule of formula (I) in which:
  $R^1$ and $R^2$, identical or different, represent an acyl group, comprising an unsaturated or saturated, acyclic carbon-containing chain,
  $R^3$ and $R^4$, identical or different, represent an acetyl group or a hydrogen atom, and
  $R^5$ represents an acyl group.

By "di-acylated MEL" is meant a molecule of formula (I) in which:
  $R^1$ and $R^2$, identical or different, represent an acyl group, comprising an unsaturated or saturated, acyclic carbon-containing chain,
  $R^3$ and $R^4$, identical or different, represent an acetyl group or a hydrogen atom, and
  $R^5$ represents a hydrogen atom.

A di-acylated MEL is thus represented by the following formula (II):

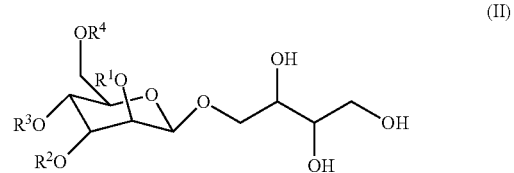

(II)

Advantageously, the at least one MEL comprised in the concentrate according to the invention is di-acylated.

Two stereoisomers of di-acylated MEL of formula (II) are known and represented in formulae (III) and (IV) below:

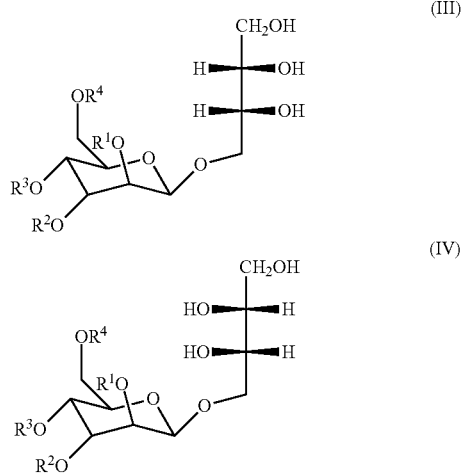

in which $R^1$, $R^2$, $R^3$, $R^4$ are identical to those indicated in formula (II).

Advantageously, a di-acylated MEL is a molecule of formula (III).

Formulae (I) to (IV) above can represent several molecules, each molecule therefore being a MEL. By "MELs" is meant at least two molecules of formulae (I), (II), (III) or (IV) different by virtue of their substitution (acyl, acetyl groups), or by virtue of their stereoisomerism, more particularly, at least two different molecules of formulae (III).

Furthermore, the MELs are generally classified in four classes of molecules, denoted A to D, according to their degree of acetylation in positions $R^3$ and $R^4$. The class of the MELs-A comprises molecules of formula (I) having two acetyl groups in positions $R^3$ and $R^4$. The class of the MELs-B and the class of the MELs-C comprise molecules of formula (I) having a single acetyl group in positions $R^4$ and $R^3$ respectively. Finally, the class of the MELs-D comprises molecules of formula (I) having no acetyl group ($R^3=R^4=H$).

As well as by their degree of acetylation, the MELs can vary in their structure, by the nature of the fatty acids of which their hydrophobic part is composed. This variation is generally a function of the process utilized for obtaining the MELs.

The MELs are generally obtained by processes utilizing the cultivation of fungi, and more particularly of yeasts.

Advantageously, the MEL(s) to which the present application relates are obtained by a fermentation process, comprising the following steps:
  cultivation of a fungi strain and more particularly of a yeast strain in the presence of a carbon source in order to obtain MELs, and
  recovery of the MELs thus obtained.

The strains from which it is possible to obtain MELs are well known to a person skilled in the art. By way of example, it is known to use strains of the family of the Basidiomycetes, preferably of the genus *Pseudozyma*, such as *Pseudozyma antarctica*, *Pseudozyma parantarctica*, *Pseudozyma aphidis*, *Pseudozyma rugulosa*, *Pseudozyma graminicola*, *Pseudozyma siamensis*, *Pseudozyma hubeiensis*, *Pseudozyma tsukubaensis*, *Pseudozyma crassa*, or of the genus *Ustilago*, such as *Ustilago maydis*, *Ustilago cynodontis* and *Ustilago scitaminea*.

In general, depending on the strain, a class of MELs (MELs-A, MELs-B, MELs-C or MELs-D) is mainly or even exclusively produced with respect to the other classes of MEL. By way of example, *Pseudozyma antarctica*, *Pseudozyma aphidis*, *Pseudozyma rugulosa* and *Pseudozyma parantarctica* produce mainly MELs-A of formula (III). *Pseudozyma graminicola*, *Pseudozyma siamensis*, *Pseudozyma hubeiensis* produce mainly MELs-C of formula (III). *Pseudozyma tsukubaensis* produces mainly MELs-B of formula (IV) and *Pseudozyma crassa* produces mainly MELs-A of formula (IV).

Advantageously, the MELs are obtained by a fermentation process utilizing a strain producing MELs of formula (III).

More particularly, the MELs are obtained by a fermentation process utilizing a strain selected from *Pseudozyma aphidis*, *Pseudozyma rugulosa* *Pseudozyma antarctica* or *Pseudozyma parantarctica*, preferentially from *Pseudozyma aphidis*, *Pseudozyma antarctica* or *Pseudozyma parantarctica*, more preferentially, the strain is *Pseudozyma aphidis*.

The carbon-containing substrate is typically a glycerol, an n-alkane or an oil, in particular of renewable origin.

Any oil, composed of triglycerides and liquid at the temperature of the fermentation process, can be used as carbon-containing substrate.

Preferentially, the renewable oil is a vegetable or animal oil, more preferentially, a vegetable oil. In particular, the vegetable oil is selected from the group constituted by a soya oil, a sunflower oil, an olive oil and a rapeseed oil. More particularly, the vegetable oil is a soya oil or a rapeseed oil, even more particularly, a rapeseed oil.

These renewable oils are particularly rich in acyl groups comprising a carbon-containing chain with 18 carbon atoms, such as the acyl groups originating from oleic, linoleic and/or linolenic acid.

The fermentation process generally lasts at least 3 days, preferentially at least 7 days.

According to a preferential embodiment, the MELs are obtained by a fermentation process utilizing:
  a strain of the genus *Pseudozyma*, preferentially *Pseudozyma antarctica*, *Pseudozyma parantarctica*, or *Pseudozyma aphidis*,
  a vegetable oil, preferentially a rapeseed oil or a soya oil, as carbon-containing substrate.

Such a strain is usually cultured in a reactor in a medium comprising glucose, water and/or salts (such as magnesium sulphate, monopotassium phosphate, sodium nitrate and/or ammonium nitrate). This culture medium is also utilized in the fermentation process. In fact, in general, the fermentation medium of the fermentation process comprises a culture medium and the carbon-containing substrate.

Advantageously, the different components of the medium (glucose and strain in particular) are sterilized separately before introduction into the reactor.

The temperature of the medium is preferably comprised between 20° C. and 40° C., more preferentially between 25° C. and 35° C.

The crude reaction medium obtained at the end of the fermentation process is what is called the crude fermentation medium in the present application.

The crude fermentation medium generally comprises at least two di-acylated MELs, at least residual carbon-containing substrate and/or a by-product of the carbon-containing substrate, the strain and water, the by-product of the carbon-containing substrate resulting from the fermentation.

The step of recovering the MELs is intended to separate one or more MEL(s) from one or more of the other components of the crude fermentation medium, such as residual carbon-containing substrate and/or a by-product of the carbon-containing substrate, a strain and/or water.

According to the preferential embodiment above, the crude fermentation medium comprises at least two di-acylated MELs, at least one triglyceride and/or at least one fatty acid, water and a strain of the genus *Pseudozyma*.

In fact, when the carbon-containing substrate is an oil of renewable origin, a by-product of the carbon-containing substrate is a fatty acid. In addition, as a vegetable oil is mainly (more than 90% by weight) constituted by triglycerides, the residual vegetable oil is thus composed of at least one triglyceride.

The separation of one or more MEL(s) from one or more of the other components of the crude fermentation medium can be carried out by any separation method known to a person skilled in the art.

Advantageously, the separation of one or more MEL(s) from one or more of the other components can comprise one or more of the following methods:
settling,
centrifugation,
filtration,
evaporation,
liquid/liquid extraction,
passing over a mineral substrate or a resin.
In particular:
the strain can be separated by settling, filtration, and/or centrifugation;
the water can be separated by settling, evaporation, centrifugation, and/or passing over a mineral substrate which is an adsorbent;
the fatty acids and the triglycerides can be separated by liquid/liquid extraction and/or by passing over a mineral substrate or a resin.
The recovered MELs can thus comprise:
at least one triglyceride and/or at least one fatty acid, and optionally, a strain.

By "fatty acid" is meant a fatty acid that is free and/or in the form of a salt.

The quantity of fatty acid(s) and/or of triglyceride(s) present in the recovered MELs can be comprised between 0.5 and 60% by weight, preferably between 1 and 50% by weight, with respect to the total weight of recovered MELs.

Advantageously, the fatty acid(s) comprise(s) a carbon-containing chain comprising between 8 and 24 carbon atoms, preferably between 8 and 20 carbon atoms.

Advantageously, the triglyceride(s) comprise(s) acyl groups the saturated or unsaturated, acyclic carbon-containing chain of which comprises between 8 and 24 carbon atoms, preferably between 16 and 18 carbon atoms. More particularly, the carbon-containing chain is linear and comprises only carbon and hydrogen atoms, optionally substituted by a hydroxyl (OH) function.

The recovered MELs can therefore be in a more or less purified form, i.e. in a mixture with other components of the fermentation medium.

More particularly, in the present application, and in particular in the examples, when the recovered MELs are in a mixture with at least one fatty acid and/or at least one triglyceride, optionally water and/or a strain, this mixture is called "mixture of MELs".

A first mixture of MELs is a crude fermentation medium, i.e. at least two di-acylated MELs with the other components of the crude fermentation medium.

The crude fermentation medium can be subjected to one or more separation methods, leading to other preferred mixtures of MELs having the following features:
a content of MELs greater than or equal to 30% by weight, preferentially greater than or equal to 40% by weight, more preferentially greater than or equal to 50% by weight;
a content of other components (including fatty acid(s), triglyceride(s), water and/or strain) less than or equal to 70% by weight, preferentially less than or equal to 60% by weight, more preferentially less than or equal to 50% by weight;
the percentages by weight being given with respect to the weight of the mixture of MELs.

More particularly, depending on the separation method(s) such as those described above, mixtures of MELs with a greater or lesser concentration of MELs can be obtained.

According to a first embodiment, the mixture of MELs has the following features:
a content of MELs greater than or equal to 55% by weight;
a content of other components (including fatty acid(s), triglyceride(s), water and/or strain) less than or equal to 45% by weight;
the percentages by weight being given with respect to the weight of the mixture of MELs.

Advantageously, in this first embodiment, the water and/or strain content is less than or equal to 10% by weight, preferentially less than or equal to 5% by weight, with respect to the weight of the mixture of MELs.

According to a second embodiment, which is particularly preferred, the mixture of MELs has the following features:
a content of MELs greater than or equal to 90% by weight, preferentially greater than or equal to 95% by weight, more preferentially greater than or equal to 98% by weight;
a content of other components (including fatty acid(s), triglyceride(s), water and/or strain) less than or equal to 10% by weight, preferentially less than or equal to 5% by weight, more preferentially less than or equal to 2% by weight; the percentages by weight being given with respect to the weight of the mixture of MELs.

Advantageously, in this second embodiment, the water and/or strain content is less than or equal to 2% by weight, with respect to the weight of the mixture of MELs.

Such a mixture of MELs can for example be obtained using a fermentation process such as described above, comprising several separation steps such as described above, these separation steps preferentially including a liquid/liquid extraction and/or passing over a mineral substrate.

Passing over a mineral substrate can be a chromatography, such as an adsorption chromatography on a silica column, carried out using suitable solvents. Such solvents are known to a person skilled in the art.

Examples of mixtures of MELs and of a process for the production thereof are also described in the following publication: "Downstream processing of mannosylerythritol lipids produced by *Pseudozyma aphidis*"; Rau et al.; European Journal of Lipids Science and Technology (2005), 107, 373-380.

Advantageously, the MEL(s) recovered at the end of the fermentation process described above is/are di-acylated.

When the MEL(s) recovered at the end of the fermentation process is/are one or more di-acylated MEL(s), it is possible to utilize a subsequent step of production of tri-acylated MELs starting from the one or more recovered di-acylated MEL(s) (or from a mixture of di-acylated MELs).

This subsequent step advantageously comprises:
dissolution of the one or more di-acylated MEL(s) in an organic solvent in the presence of an enzyme; and
addition of at least one vegetable oil, at least one fatty acid of vegetable origin or at least one fatty acid ester of vegetable origin;
under conditions allowing either a transesterification reaction between the di-acylated MEL(s) and the triglycerides present in the vegetable oil or the fatty acid ester of vegetable origin, or an esterification reaction between the di-acylated MEL(s) and the fatty acid of vegetable origin, thus allowing the production of tri-acylated MEL(s).

Advantageously, the organic solvent is selected from methanol, ethanol, propanol, butanol, acetone, propanone, butanone, pentan-2-one, 1,2-ethanediol, 2,3-butanediol, dioxane, acetonitrile, 2-methyl-butan-2-ol, tert-butanol, 2-methylpropanol, 4-hydroxy-2-methyl pentanone, tetrahydrofuran, hexane, dimethylformamide (DMF), dimethylsulphoxide (DMSO) and/or pyridine.

Preferentially, the vegetable oil is selected from the group constituted by a soya oil, a sunflower oil, an olive oil and a rapeseed oil. More particularly, the vegetable oil is a soya oil or a rapeseed oil, even more particularly, a rapeseed oil.

Advantageously, the fatty acid of vegetable origin or the fatty acid ester of vegetable origin originates from a soya oil, a sunflower oil, an olive oil or a rapeseed oil. More particularly, the fatty acid of vegetable origin or the fatty acid ester of vegetable origin originates from a soya oil or a rapeseed oil, even more particularly, from a rapeseed oil.

These vegetable oils are particularly rich in acyl groups comprising a carbon-containing chain with 18 carbon atoms, such as in the acyl groups originating from oleic, linoleic and/or linolenic acid.

The enzyme can be selected from lipases, proteases and/or esterases, preferably from lipases and/or esterases, even more preferentially from lipases.

Advantageously, the esterification or transesterification reaction is carried out during approximately 12 to 72 hours at a temperature close (+/−10° C.) to the optimal temperature of activity of the enzyme, preferably during approximately 24 to 48 hours at a temperature comprised between 20 and 30° C., more preferentially at 25° C.

The tri-acylated MEL(s) can then be recovered from the reaction medium, by separation methods known to a person skilled in the art.

For example chromatography, such as adsorption chromatography on a silica column, is included among these separation methods.

The concentrate according to the invention also comprises at least 30% by weight of at least one polyglycerol fatty acid ester, with respect to the total weight of the concentrate.

Preferably, the concentrate according to the invention comprises a polyglycerol fatty acid ester.

Advantageously, the fatty acid comprised in the polyglycerol fatty acid ester comprises a carbon-containing chain comprising between 6 and 18 atoms.

As the polyglycerol fatty acid ester is intended to be solubilized in water, it is hydrophilic, advantageously with an HLB greater than or equal to 9, preferentially greater than or equal to 10, more preferentially greater than or equal to 12.

By HLB (Hydrophilic-Lipophilic Balance) is meant the balance between the dimension and the force of the hydrophilic group and the dimension and the force of the lipophilic group of the surfactant. The HLB value according to GRIFFIN is defined in J. Soc. Cosm. Chem. 1954 (Volume 5), pages 249-256.

By way of example of polyglycerol fatty acid esters having an HLB greater than or equal to 9, there may be mentioned polyglycerol-6 isostearate, polyglycerol-10 isostearate, polyglycerol-10 diisostearate, polyglycerol-6 laurate, polyglycerol-6 myristate, polyglycerol-6 stearate, polyglycerol-6 oleate, polyglycerol-10 oleate, polyglycerol-10 caprylate, polyglycerol-6 caprylate, polyglycerol-4 caprate, polyglycerol-4 laurate, polyglycerol-10 laurate.

Preferably, the polyglycerol comprised in the polyglycerol fatty acid ester comprises between 2 and 12, preferably between 2 and 10, more preferentially between 3 and 6 units of glycerol.

Advantageously, the polyglycerol of the polyglycerol fatty acid ester is a polyglycerol-4, polyglycerol-6 or polyglycerol-10. The integer following the polyglycerol (or PG) represents the number of glycerol units forming the polyglycerol.

Preferentially, the polyglycerol fatty acid ester is a polyglycerol fatty acid monoester or a polyglycerol fatty acid diester, more preferentially a polyglycerol fatty acid monoester.

The concentrate according to the invention has a good thickening property. By "thickening property" is meant that the concentrate according to the invention increases the viscosity of water. In other words, a composition comprising a concentrate according to the invention and water will have a viscosity greater than that of water alone, advantageously of at least 30 mPa·s, preferably of at least 80 mPa·s, more preferentially of at least 200 mPa·s, even more preferentially of at least 300 mPa·s.

Moreover, the concentrate according to the invention makes it possible to give water the appearance of a gel, i.e. that a composition comprising a concentrate according to the invention and water will present the appearance of a gel.

By "gel appearance" is meant the typical rheology of a gel. In particular, the initial viscosity of a composition comprising a concentrate according to the invention and water will decrease if it is subjected to friction, and will return to its initial value once the friction has ceased.

These features of the concentrate according to the invention are described in greater detail in Example 2 below.

Furthermore, the concentrate according to the invention has a good foaming property. It is understood here that, when placed in contact with water, a concentrate according to the invention allows the formation of a foam on the surface of the composition obtained.

Preferably, the concentrate according to the invention allows the formation of a foam under conditions similar to those described in standard ASTM D892.

In the present application, any reference to a standard is a reference to the standard current at the date of filing.

Advantageously, the volume of the foam formed on the surface of a composition comprising a concentrate according to the invention and water is greater than 200 mL, preferably greater than 400 mL, even more preferentially greater than 600 mL. Such a volume varies as a function of the hardness of the water.

Furthermore, the foam formed on the surface of a composition comprising a concentrate according to the invention is stable. By "stable" is meant that the volume of foam formed does not decrease or decreases very little over time, i.e. by less than 50 mL in 10 min, preferentially less than 25 mL in 10 min.

The foaming property of the concentrate according to the invention as well as the stability of a foam formed on the surface of a composition comprising the concentrate according to the invention are described in greater detail in Example 3.

Moreover, the concentrate according to the invention has a good cleaning property. Advantageously, the concentrate according to the invention comprises at least 30% by weight, optionally at least 45% by weight of at least one MEL, with respect to the total weight of the concentrate.

Advantageously, at least 80% by weight of the concentrate according to the invention is constituted by mannosylerythritol lipid(s) and polyglycerol fatty acid ester(s).

Preferably, in the concentrate according to the invention, the ratio by weight of mannosylerythritol lipid(s) and polyglycerol fatty acid ester(s) is comprised within the range [1/2; 2/1].

Such a ratio makes it possible to further improve the thickening property of the concentrate according to the invention.

Preferably, the at least one polyglycerol fatty acid ester comprised in the concentrate according to the invention is a polyglycerol capric and/or caprylic acid ester.

A polyglycerol capric and/or caprylic acid ester is also called polyglycerol caprate and/or caprylate, or polyglyceryl caprate and/or caprylate.

Preferably, the at least one ester is a polyglycerol capric acid ester.

Alternatively, the at least one polyglycerol fatty acid ester is a polyglycerol fatty acid ester comprising 18 carbon atoms, preferably a polyglycerol oleic or isostearic acid ester.

Advantageously, the concentrate according to the invention comprises at least two MELs, in particular at least two MELs originating from different classes, selected from the group constituted by the MELs-A, MELs-B, MELs-C and MELs-D.

According to a first advantageous embodiment, the concentrate according to the invention comprises MELs-A, MELs-B, MELs-C and optionally MELs-D, more preferentially MELs-A, MELs-B, MELs-C and MELs-D.

Advantageously, the concentrate according to the invention comprises MELs-A and MELs-B at a content comprised between 50% and 95% by weight, preferably 60% to 85% by weight, the percentages by weight being indicated with respect to the weight of the total quantity of MELs.

Advantageously, the concentrate according to the invention comprises MEL(s)-C at a content greater than or equal to 5% by weight, preferentially greater than 10% by weight, the percentages by weight being indicated with respect to the weight of the total quantity of MELs.

More particularly, the concentrate according to the invention comprises MELs-A and MELs-B at a content comprised between 60% and 80% by weight and MELs-C at a content greater than or equal to 15% by weight, the percentages by weight being indicated with respect to the weight of the total quantity of MELs.

According to a second advantageous embodiment, the concentrate according to the invention comprises MELs-D at a content comprised between 75% and 100% by weight, preferably between 90% and 100% by weight, the percentages by weight being indicated with respect to the weight of the total quantity of MELs.

The MELs-D can be obtained by deacetylation of the MELs-A, MELs-B and MELs-C. An example of a deacetylation reaction of the MELs-A, MELs-B and MELs-C using a hydrolyzing enzyme is described in the following publication: "Enzymatic synthesis of a novel glycolipid biosurfactant, mannosylerythritol lipid-D and its aqueous phase behavior"; Fukuoka et al.; Carbohydrate Research (2011), 346, 266-271.

Advantageously, the concentrate according to the invention also comprises at least one glycerol fatty acid ester.

Preferably, the concentrate according to the invention comprises a glycerol fatty acid ester.

According to a first embodiment of the concentrate according to the invention, the latter comprises or consists of:
  at least 20% by weight of at least one mannosylerythritol lipid, with respect to the total weight of the concentrate, and
  at least 30% by weight of at least one polyglycerol fatty acid ester, with respect to the total weight of the concentrate,
  in which the ratio by weight of mannosylerythritol lipid(s)/polyglycerol fatty acid ester(s) is comprised within the range [1/3; 3/1].

According to a second embodiment of the concentrate according to the invention, the latter comprises or consists of:
  at least 20% by weight of at least one mannosylerythritol lipid, with respect to the total weight of the concentrate,
  at least 30% by weight of at least one polyglycerol fatty acid ester, with respect to the total weight of the concentrate, and
  at least one glycerol fatty acid ester,
  in which the ratio by weight of mannosylerythritol lipid(s)/polyglycerol fatty acid ester(s) is comprised within the range [1/3; 3/1].

The at least one polyglycerol fatty acid ester utilized in these two embodiments is advantageously a polyglycerol capric and/or caprylic acid ester, preferably a polyglycerol capric acid ester.

Advantageously, in the concentrate according to the invention, the quantity of glycerol fatty acid ester(s) is comprised between 1.5% and 4.5% by weight, preferably between 2 and 4% by weight of the total weight of the concentrate.

The above-described preferred features of the concentrate according to the invention are applicable to these embodiments as a whole.

Preferably, the at least one glycerol fatty acid ester comprised in the concentrate according to the invention is a glycerol caprylic acid ester.

When added to water, the glycerol caprylic acid ester causes a bloom effect in water. This effect is very beneficial for developing cosmetic products, such as those for which it is desired to obtain a milky texture.

A composition, such as a cosmetic composition, prepared from a concentrate according to the invention comprising glycerol caprylic acid ester will have advantageous properties, such as a pleasant feel without an oily film, and gives the user a sensation of skin nourishment.

Glycerol caprylic acid esters also have good antimicrobial properties.

The invention also relates to a process for the preparation of a concentrate according to the invention, comprising a step of mixing at least 20% by weight of at least one mannosylerythritol lipid, with respect to the total weight of the concentrate, and at least 30% by weight of at least one polyglycerol fatty acid ester, with respect to the total weight of the concentrate, in which the ratio by weight of mannosylerythritol lipid(s)/polyglycerol fatty acid ester(s) is comprised within the range [1/3; 3/1].

Advantageously, the mixture is produced at a temperature comprised between 40 and 60° C., preferably 60° C.

Advantageously, the components utilized in the process for the preparation of a concentrate according to the invention have one or more of the above-described preferred features.

The invention further relates to a composition comprising a concentrate according to the invention, and water. More particularly, the composition according to the invention comprises:
at least one MEL,
at least one polyglycerol fatty acid ester having an HLB greater than or equal to 9, and
water,
in which the ratio by weight of mannosylerythritol lipid(s)/polyglycerol fatty acid ester(s) having an HLB greater than or equal to 9 is comprised within the range [1/3; 3/1].

The at least one MEL and the at least one polyglycerol fatty acid ester are such as described above, including the advantageous and preferential modes.

The composition according to the invention has a good cleaning, and more particularly makeup removal, property. This is described in greater detail in Example 6 below.

According to a first embodiment, the quantity of concentrate or the total quantity of MEL(s) and polyglycerol fatty acid ester(s) having an HLB greater than or equal to 9 in the composition according to the invention is comprised between 3% and 75% by weight of the total weight of the composition.

By total quantity of MEL(s) and polyglycerol fatty acid ester(s) having an HLB greater than or equal to 9 is meant the total quantity by weight of molecules of MEL(s) and molecules of polyglycerol fatty acid ester(s).

According to this first embodiment of the composition according to the invention, the latter has a viscosity much greater than that of water, and has the appearance of a gel.

According to a particular mode of this first embodiment, the composition according to the invention comprises a concentrate according to the invention that has no glycerol fatty acid ester. In this particular mode, when the quantity of concentrate or the total quantity of MEL(s) and polyglycerol fatty acid ester(s) having an HLB greater than or equal to 9 comprised in the composition according to the invention is small, i.e. comprised between 3% and 7% by weight of the total weight of the composition, it is preferable for the concentrate or the total quantity of MEL(s) and polyglycerol fatty acid ester(s) having an HLB greater than or equal to 9 to comprise at least 50% by weight of at least one MEL, with respect to the total weight of concentrate or of the total quantity of MEL(s) and polyglycerol fatty acid ester(s) having an HLB greater than or equal to 9, respectively. Such a MEL content makes it possible to obtain a notable increase in the viscosity of water.

According to a particular alternative mode of this first embodiment, the composition according to the invention comprises at least one glycerol fatty acid ester. In this particular mode, a notable increase in the viscosity of water is obtained even at a content of at least 20% by weight of MEL(s) with respect to the total weight of concentrate or of the total quantity of MEL(s) and polyglycerol fatty acid ester(s) having an HLB greater than or equal to 9.

According to this first embodiment, the quantity of concentrate or the total quantity of MEL(s) and polyglycerol fatty acid ester(s) having an HLB greater than or equal to 9 in the composition according to the invention is advantageously comprised between 5 and 50% by weight, preferably between 5 and 35% by weight, of the total weight of the composition.

Increasing concentrate contents make it possible to increase the viscosity of the composition according to the invention. A person skilled in the art is capable of defining or adapting the quantity of concentrate in the composition making it possible to obtain a desired viscosity.

According to this embodiment, the composition according to the invention advantageously has a dynamic viscosity greater than or equal to 40 mPa·s, preferably greater than or equal to 200 mPa·s, more preferentially greater than or equal to 400 mPa·s, even more preferentially greater than or equal to 500 mPa·s.

According to a second embodiment, the quantity of concentrate in the composition according to the invention, expressed as a percentage by weight of the total weight of the composition, is comprised within the range [0.05; 3)

According to this second embodiment of the composition according to the invention, the latter has a viscosity that is not much greater than that of water, and is presented in the form of a solution.

According to this second embodiment, the quantity of concentrate is advantageously comprised between 0.1 and 2% by weight, preferably between 0.15 and 1.5% by weight, with respect to the total weight of the composition.

The invention also relates to a process for the preparation of a composition according to the invention, comprising a step of mixing a concentrate according to the invention with water.

According to a first embodiment of the process for the preparation of a composition according to the invention, the at least one MEL is mixed with at least one polyglycerol fatty acid ester having an HLB greater than or equal to 9, before mixing with water.

According to a second embodiment of the process for the preparation of a composition according to the invention, the at least one MEL is mixed with water independently of a polyglycerol fatty acid ester.

Advantageously, the mixing step is carried out under stirring.

The invention also relates to the use of a concentrate according to the invention as a thickening, foaming and/or cleaning agent.

The concentrate according to the invention can be used in any type of application in which it is usual to use a thickening, foaming and/or cleaning agent.

This concentrate can be used as a thickening, foaming and/or cleaning agent in the preparation of cleaning or detergent products such as household or industrial maintenance compositions, in particular compositions for cleaning hard surfaces, or dishwashing products.

This concentrate can also be used in cleaning products in the petroleum industry.

Finally, this concentrate can be used as a thickening, foaming and/or cleaning agent in cosmetics or hygiene products.

The invention also relates to the use of a composition according to the invention as a cleaning composition.

The composition according to the invention can be used in any type of application in which it is usual to use cleaning compositions.

By way of example, the composition according to the invention can be used as a cleaning or detergent composition, for example as a household or industrial maintenance composition, in particular as a composition for cleaning hard surfaces, or as a dishwashing product.

The composition according to the invention can also be used in the petroleum industry.

Advantageously, the composition according to the invention is used as a hygiene product or in cosmetics, preferably as a washing and/or makeup removal composition.

This composition can be used in order to form a lather with water, or can be applied directly to the skin without adding water.

In particular, the composition according to the invention in the first embodiment thereof, as described above, has the appearance of a gel, and will therefore advantageously be used to form a lather with water.

For example, the user may apply water to the part of the body to be cleaned, then apply the composition according to the invention to this part, and finally rub in order to lather said composition.

The composition according to the invention in the first embodiment thereof may also be used as a base for a hygiene product such as a micellar gel.

The composition according to the invention in the second embodiment thereof, as described above, is in the form of a solution, and thus will advantageously be applied directly to the skin, such as the skin of the face, for example using a cotton pad.

By "solution" is meant a liquid having a dynamic viscosity at 25° C. less than 40 mPa·s.

The invention also relates to the use of a concentrate according to the invention, partially or totally replacing a surfactant selected from the group constituted by sodium lauryl sulphate, sodium lauryl ether sulphate and/or cocamide diethanolamine.

Figure 2:
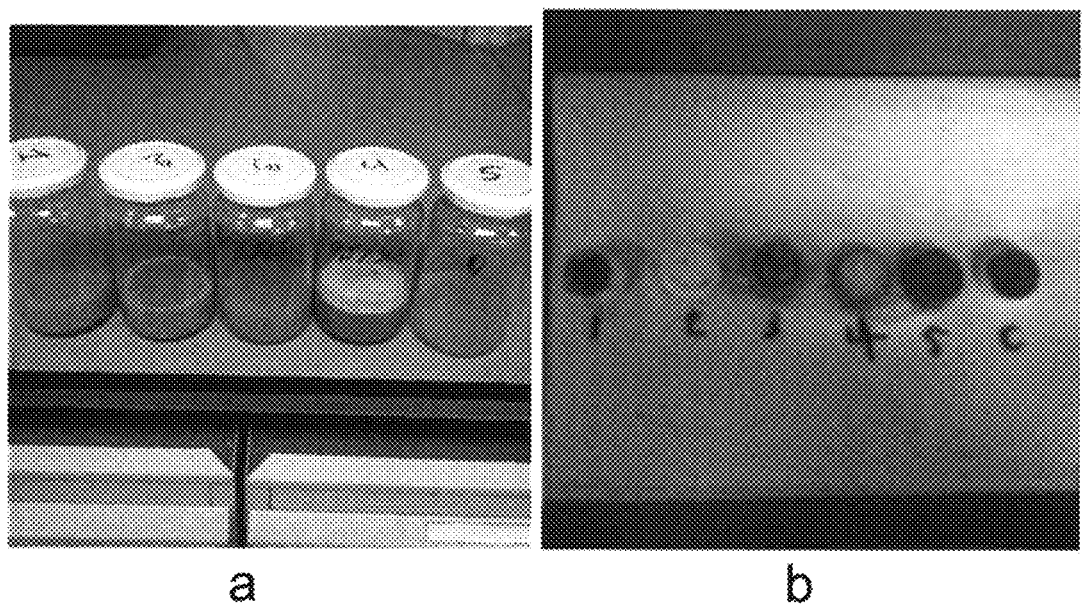

The invention will be better understood in the light of the following examples, given by way of illustration, with reference to the following figures:

FIG. 1, which is a diagram representing the stability over time of foams formed on the surface of compositions prepared from concentrates according to the invention and starting from sulphated compounds or from MELs;

FIG. 2, which comprises 2 photographs, a and b, illustrating the cleaning property of a composition according to the invention and of comparative compositions.

EXAMPLE 1: PREPARATION OF CONCENTRATES ACCORDING TO THE INVENTION

1. Obtaining MELs

The MELs were obtained by a fermentation process comprising the following steps:
 culturing a yeast strain such as *Pseudozyma aphidis* in the presence of a vegetable oil (rapeseed) in order to obtain the MELs; and
 recovering the MELs thus obtained.

At the end of the step of recovering the MELs, a first mixture of MELs (mixture of MELs 1A) is obtained, which has the following features:
 Content of MELs: 55% by weight
 Content of other components: 45% by weight (including 42% by weight of free fatty acids and triglycerides and 3% by weight of water and strain),
the percentages by weight being given with respect to the total weight of the mixture of MELs obtained.

A step of purification of the mixture of MELs 1A was then carried out by adsorption chromatography on a silica column, with the use of a mixture of solvents having an increasing polarity gradient. A second mixture of MELs (mixture of MELs 1B) was thus obtained, which has the following features:
 Content of MELs: at least 98% by weight with respect to the total weight of the mixture of MELs obtained.

In particular, each of the mixtures of MELs 1A and 1B comprises MELs-A at a content of 52% by weight, MELs-B at a content of 12% by weight, MELs-C at a content of 35% by weight, and MELs-D at a content of 1% by weight, the percentages by weight being given with respect to the weight of the total quantity of MELs.

2. Polyglycerol Fatty Acid Esters

Radia® 7932 from OLEON was used. This product is composed of polyglycerol-4 capric acid esters (polyglycerol-4 caprate or polyglyceryl-4 caprate). The purity thereof in polyglycerol fatty acid esters is greater than 95%.

Polyglycerol-10 oleic, capric and isostearic acid esters were prepared according to the esterification process with a fatty acid (oleic acid, Radiacid 0215 from OLEON, capric acid, Radiacid 610 from OLEON and isostearic acid, Radiacid 0909 from OLEON) and polyglycerol-10 from SPIGA NORD, in a 1/1 molar ratio. The fatty acid and polyglycerol are mixed in the presence of calcium hydroxide and heated at 220° C. until the acid number is less than 1 mgKOH/g.

3. Glycerol Fatty Acid Ester

Radia® 7907 from OLEON was used. This product is composed of glycerol caprylic acid esters (glycerol monocaprylate or glyceryl monocaprylate).

4. Preparation of Concentrates According to the Invention

The compounds are mixed manually in a suitable vessel, according to the formulations indicated in Table 1 hereinafter at a temperature of 60° C., until homogenization of the concentrate. Preferably, the temperature should not exceed 60° C.

The different concentrates prepared are summarized in the following Table 1:

TABLE 1

Concentrates according to the invention prepared in Example 1

|  | Mixture of MELs 1B (%) | Radia® 7932 (%) | Radia® 7907 (%) | PG-10 Oleate | PG-10 caprylate | PG-10 isostearate |
|---|---|---|---|---|---|---|
| Concentrate 1 | 25 | 75 | — | | | |
| Concentrate 2 | 33.3 | 66.7 | — | | | |
| Concentrate 3 | 50 | 50 | — | | | |
| Concentrate 4 | 66.7 | 33.3 | | | | |
| Concentrate 5 | 25 | 70.8 | 4.2 | | | |
| Concentrate 6 | 33.3 | 62.9 | 3.8 | | | |
| Concentrate 7 | 50 | 47.2 | 2.8 | | | |
| Concentrate 8 | 66.7 | 31.44 | 1.86 | | | |
| Concentrate 15 | 50 | | 2.8 | 47.2 | | |

TABLE 1-continued

Concentrates according to the invention prepared in Example 1

|  | Mixture of MELs 1B (%) | Radia® 7932 (%) | Radia® 7907 (%) | PG-10 Oleate | PG-10 caprylate | PG-10 isostearate |
|---|---|---|---|---|---|---|
| Concentrate 16 | 50 |  | 2.8 |  | 47.2 |  |
| Concentrate 17 | 50 |  | 2.8 |  |  | 47.2 |

*The percentages indicated are percentages by weight with respect to the total weight of concentrate.

EXAMPLE 2: EVALUATION OF THE THICKENING PROPERTY OF THE CONCENTRATES ACCORDING TO THE INVENTION AND OF COMPARATIVE CONCENTRATES

The thickening property of the concentrates according to the invention and of comparative concentrates was evaluated.
1. Equipment and Methods
1.1. Equipment
The following products were used:
concentrates 1 to 8 prepared in Example 1
the mixture of MELs 1B prepared in Example 1
Radia® 7932 (OLEON)
Radia® 7907 (OLEON)
demineralized water
The following equipment was used:
glass flasks
a spatula
a rheometer (TA Instruments AR 2000).
1.2. Methods
Concentrates According to the Invention
Concentrates 1 to 8 prepared in Example 1 were used.
Preparation of the Comparative Concentrates
The different compounds are mixed manually in a suitable vessel, at a temperature of 60° C., until the concentrate is homogenized. When MELs are used in the preparation of the concentrate, the temperature preferably should not exceed 60° C.
The different comparative concentrates prepared are summarized in the following Table 2.

TABLE 2

Comparative concentrates prepared in Example 2

|  | Mixture of MELs 1B (%) | Radia® 7932 (%) | Radia® 7907 (%) |
|---|---|---|---|
| Comparative concentrate 9 | 0 | 100 | — |
| Comparative concentrate 10 | 10 | 90 | — |
| Comparative concentrate 11 | 100 | 0 | — |
| Comparative concentrate 12 | 0 | 94.4 | 5.6 |
| Comparative concentrate 13 | 10 | 84.96 | 5.04 |
| Comparative concentrate 14 | 15 | 80.24 | 4.76 |

*The percentages indicated are percentages by weight with respect to the total weight of concentrate.

Evaluation of the Thickening Property of Concentrates 1 to 14

10% by weight of concentrates 1 to 8 according to the invention and comparative concentrates 9 to 14 were respectively added to 90% by weight of water in glass flasks, the % by weight being indicated with respect to the total weight of each composition obtained. The addition of water in the flasks containing the different concentrates is carried out under manual stirring with a spatula.

The dynamic viscosity of compositions 1 to 14 was evaluated, using a rheometer, at a temperature of 25° C. and at a speed of 10 rpm.

The dynamic viscosity of the water (control) is 1 mPA.s.

The appearance of the different compositions was also evaluated by the naked eye.

The results are presented in Table 3 hereinafter.

TABLE 3

Dynamic viscosity and appearance of compositions 1 to 14 prepared in Example 2

|  |  | Viscosity (mPa · s) | Appearance |
|---|---|---|---|
| Composition 1 according to the invention | Concentrate 1 according to the invention + water | 44 | Partial gel appearance, one phase |
| Composition 2 according to the invention | Concentrate 2 according to the invention + water | 48 | Partial gel appearance, one phase |
| Composition 3 according to the invention | Concentrate 3 according to the invention + water | 586 | Gel appearance, one phase |
| Composition 4 according to the invention | Concentrate 4 according to the invention + water | 980 | Gel appearance, one phase |
| Composition 5 according to the invention | Concentrate 5 according to the invention + water | 56 | Gel appearance, one phase |
| Composition 6 according to the invention | Concentrate 6 according to the invention + water | 400 | Gel appearance, one phase |
| Composition 7 according to the invention | Concentrate 7 according to the invention + water | 500 | Gel appearance, one phase |
| Composition 8 according to the invention | Concentrate 8 according to the invention + water | 70 | Gel appearance, one phase |
| Comparative composition 9 | Comparative concentrate 9 + water | 5 | Clear water appearance |
| Comparative composition 10 | Comparative concentrate 10 + water | 13 | Two phases |
| Comparative composition 11 | Comparative concentrate 11 + water | 5 | Two phases |
| Comparative composition 12 | Comparative concentrate 12 + water | 5.5 | Clear water appearance |
| Comparative composition 13 | Comparative concentrate 13 + water | 4.5 | 1 phase, cloudy, translucent |
| Comparative composition 14 | Comparative concentrate 14 + water | >5 | 1 phase, cloudy, translucent |

The results show that compositions 1 to 8 comprising a concentrate according to the invention and water have a dynamic viscosity greater than that of pure water, and also have the appearance of a gel. On the other hand, compositions 9 to 14 comprising comparative concentrates have a viscosity close to that of water and do not have the appearance of a gel.

A concentrate according to the invention makes it possible to increase the viscosity of water. It is understood here that a composition comprising a concentrate according to the invention and water will have a viscosity greater than that of water alone.

The concentrate according to the invention thus has a good thickening property, and therefore can be used as a thickening agent.

Moreover, a concentrate according to the invention makes it possible to give water the appearance of a gel.

EXAMPLE 3: EFFECT OF THE QUANTITY OF CONCENTRATE ON THE VISCOSITY OF WATER

Compositions comprising different quantities of concentrate 2 according to the invention prepared in Example 1 and water were prepared according to the method described in Example 2.

Viscosity measurements were carried out, in the same way as in Example 2.

The results are shown in Table 4 hereinafter.

TABLE 4

Effect of the quantity of concentrate on the viscosity of water

| Quantity of concentrate (%) | Quantity of water (%) | Viscosity (mPa · s) |
|---|---|---|
| 1 | 99 | 7 |
| 3 | 97 | 9 |
| 5 | 95 | 18 |
| 10 | 90 | 48 |
| 15 | 85 | 141 |
| 20 | 80 | 175 |
| 30 | 70 | 981 |
| 50 | 50 | 4380 |

*The percentages indicated are percentages by weight with respect to the total weight of the composition.

The results show that increasing quantities of concentrates according to the invention make it possible to increase the viscosity of water.

EXAMPLE 4: EVALUATION OF THE FOAMING PROPERTY OF A CONCENTRATE ACCORDING TO THE INVENTION AND OF COMPARATIVE CONCENTRATES—EVALUATION OF THE STABILITY OF THE FOAMS OBTAINED

1. Equipment and Methods
1.1. Equipment
The following products were used:
concentrate 7 according to the invention prepared in Example 1
concentrates 15 and 16 prepared in Example 1
comparative concentrate 11 prepared in Example 2
SLES
water.

The following equipment was used:
water bath,
flow meter,
a device for streaming air at 94 mL/min.
1.2. Methods
The protocol implemented is based on that described in standard ASTM D892.

0.02%, 0.2% and 2% by weight of the concentrate 7 and respectively 99.98%, 99.8% and 98% by weight of water were added to test tubes, in order to obtain 3 compositions to be tested. Respectively 2% by weight of concentrates 15 and 16 were introduced into another two tubes, as well as 98% by weight of water.

The test tubes were then placed in a temperature-controlled bath. After 15 minutes, the desired temperature of 25° C. was reached.

Air was then pumped through a porous spherical stone diffuser in each composition to be tested. Thus small air bubbles are created, which form a dispersion of air in water. A foam is formed if the gas bubbles rise to the surface and are not broken beforehand. The gas-filled bubbles have walls of fine liquid lamellae. The compositions to be tested are maintained at a temperature of 25° C., and are subjected to air pumping for 5 minutes. The airflow is then stopped.

The volume of foam formed on the surface of each of the compositions obtained from concentrate 7, from concentrate 15 and from concentrate 16 was evaluated, directly after stopping the airflow.

The time necessary for the foam to break up is observed for the compositions comprising 0.2% and 2% by weight of concentrate 7, as well as for the compositions comprising respectively 2% by weight of concentrate 15 and 2% by weight of concentrate 16. More particularly, the stability of the foam on the surface of this composition was evaluated by measuring the volume of foam as a function of time. More specifically, the volume of foam was evaluated during 10 minutes after formation thereof, at time intervals of 60 seconds.

Throughout the entire time necessary for the measurements, the compositions to be tested are maintained at a temperature of 25° C.

An identical test was carried out for compositions to be tested comprising 0.2% by weight of comparative concentrate 11 (MELs), 0.2% and 0.5% by weight of sodium lauryl ether sulphate (SLES) and respectively 99.8%, 99.8% and 99.5% by weight of water, with respect to the total weight of the composition. SLES is used as a reference. SLES is a surfactant having very good foaming and detergent (cleaning) properties.

2. Results
Foaming Property
The results are presented in Table 5 hereinafter.

TABLE 5

Foaming property of concentrates 7, 15 and 16 according to the invention and of comparative concentrate 11 and of SLES

| Concentrate | Quantity of concentrate (%) | Quantity of water (%) | Volume of foam formed (mL) |
|---|---|---|---|
| 7 | 0.02 | 99.98 | 210 |
|  | 0.2 | 99.8 | 500 |
|  | 2 | 98 | 700 |
| 15 | 2 | 98 | 760 |
| 16 | 2 | 98 | 700 |
| 11 | 0.2 | 99.8 | 600 |
| SLES | 0.2 | 99.8 | 500 |
| SLES | 0.5 | 99.5 | 700 |

These results show that the volumes of foam formed on the surface of the compositions comprising concentrates 7, 15 or 16 according to the invention are large.

A concentrate according to the invention thus has a very good foaming property. It is understood here that when a concentrate according to the invention is placed in contact with water, it allows the formation of a large volume of foam on the surface of the composition obtained.

Moreover, the composition to be tested comprising 0.2% by weight of concentrate 7 according to the invention made it possible to obtain a foam having a volume similar to a foam obtained with a composition comprising 0.2% by weight of sodium lauryl ether sulphate and 99.8% by weight of water, with respect to the total weight of the composition.

A concentrate according to the invention is a good replacement solution for sodium lauryl ether sulphate, or for sodium lauryl sulphate.

Stability of the Foams

The results are presented in FIG. 1.

These results show that the foams obtained with concentrates 7, 15 and 16 according to the invention were stable during the 10 minutes of the test, i.e. the volume of these foams did not decrease or decreased very little in 10 minutes.

The foams obtained with SLES, in particular that obtained from the composition comprising 0.2% by weight of SLES, were less stable during the 10 minutes of the test, a reduction in the volume of these foams being visible in FIG. 1.

Thus, the foam formed on the surface of a composition comprising a concentrate according to the invention is stable. By "stable" is meant that the volume of foam formed does not decrease or decreases very little over time, i.e. by less than 50 mL in 10 min, preferentially less than 25 mL in 10 min.

Although the composition comprising 0.2% by weight of comparative concentrate 11 forms a large volume of foam, this volume is not stable and drops rapidly (−100 mL in 1 minute, −350 mL in 10 minutes), as can be seen in FIG. 1.

EXAMPLE 5: EVALUATION OF THE SURFACE-ACTIVE PROPERTY OF CONCENTRATES ACCORDING TO THE INVENTION AND OF COMPARATIVE CONCENTRATES

1. Equipment and Methods 1.1. Equipment

Concentrates 3 and 7 according to the invention prepared in Example 1

Pure water

KRUSS K100 tensiometer 1.2. Methods

Surface Tensions

Concentrates 3 and 7 according to the invention were added at different concentrations to pure water and measurements of surface tensions were taken.

The surface tension was measured using the tensiometer, using the Wilhelmy plate method.

The surface tension of the pure water was also measured. It is 71.4 mN/m.

The results are shown in Table 6 hereinafter.

TABLE 6

Surface tensions

| Concentrate | Quantity of concentrate in water (%) | Surface tension (mN/m) |
|---|---|---|
| 3 | 0.02 | 27.6 |
| 3 | 0.2 | 27.6 |
| 3 | 2 | 27.3 |

*The percentages indicated are percentages by weight with respect to the total weight of the composition.

The results presented in Table 6 show in particular that a concentrate according to the invention makes it possible to reduce the surface tension of water. A concentrate according to the invention can thus for example be used in cleaning applications.

Interfacial Tensions

Concentrates 3 and 7 according to the invention, followed by mineral oil, were added at different concentrations to pure water, and measurements of interfacial tensions were taken.

The interfacial tension of a water/mineral oil preparation was also measured. It is approximately 43 mN/m.

The results are shown in Table 7 hereinafter.

TABLE 7

Interfacial tensions

| Concentrate | Quantity of concentrate in water (%) | Interfacial tension (mN/m) |
|---|---|---|
| 3 | 0.02 | 1.1 |
| 3 | 0.2 | 0.6 |
| 3 | 2 | 0.2 |
| 7 | 0.02 | 1.1 |
| 7 | 0.2 | 0.6 |
| 7 | 2 | 0.2 |

*The percentages indicated are percentages by weight with respect to the total weight of the composition.

The values for interfacial tensions obtained with the concentrates according to the invention are sufficiently low for a concentrate according to the invention to have the capacity to disperse a mineral oil in water. A concentrate according to the invention can thus for example be used in cleaning applications.

EXAMPLE 6: CLEANING PROPERTY OF A COMPOSITION ACCORDING TO THE INVENTION—APPLICATION IN COSMETICS

1. Equipment and Methods 1.1. Equipment

The following products were used:

composition 7 according to the invention prepared in Example 2 composition 3 according to the invention prepared in Example 2 sodium lauryl sulphate (VWR®, 100% pure)

water.

The following equipment was used:

glass jars with lids, white caps of 15-mL bottles makeup (foundation, True Match™, Super Blendable Makeup, L'OREAL®).

1.2. Methods

Water and the composition to be tested were added to a glass jar.

A white cap is then covered with makeup, then immersed in the glass jar. The glass jar is closed with its lid and then subjected to stirring at 244 rpm for 60 minutes.

At the end of 60 minutes, the proportion of makeup that was removed from the cap and transferred to the mixture of water/composition to be tested is measured.

The percentage of makeup removed is calculated according to the following formula:

100−(weight of makeup on the cap before the experiment−weight of makeup on the cap after the experiment)×100/weight of makeup on the cap before the experiment.

In Experiment 1 below, this method was utilized in order to evaluate the makeup removal property of composition 7 according to the invention prepared in Example 2 and of comparative compositions. The comparative compositions comprise SLS. Like SLES, SLS is a surfactant having very good foaming and detergent (cleaning) properties.

In Experiment 2 below, this method was utilized in order to evaluate the makeup removal property of composition 3 according to the invention prepared in Example 2.

Experiment 1

The detail of the tests carried out and the results are presented in Table 8 hereinafter.

TABLE 8

Tests and results of Experiment 1

| Test | Composition to be tested | % of makeup removed |
|---|---|---|
| Test 1 | 1 g of composition 7 according to the invention in 49 g of water | 95.92 |
| Test 2 | 5 g of composition 7 according to the invention in 49 g of water | 99.07 |
| Comparative test 3 | 0.05 g of sodium lauryl sulphate in 50 g of water | 90.70 |
| Comparative test 4 | 0.25 g of sodium lauryl sulphate in 50 g of water | 98.37 |
| Test 5 (control) | Water alone | 71.72 |

The results of Experiment 1 are also presented in FIG. 2 (comprising photographs a and b).

It can be seen in the photograph that the proportion of makeup that was removed from the cap and transferred to the mixture of water/composition 7 according to the invention (glass jars marked 1 and 2) is greater than that removed from the caps and transferred into the water/comparative composition mixtures (glass jars marked 3 and 4) and into water alone (glass jar marked 5).

This is also apparent from photograph b, which shows the quantity of makeup that was removed from the caps at the end of each test 1 to 5.

The cap numbered 0 in photograph b corresponds to a control cap before insertion in a glass jar.

These results show that composition 7 according to the invention has a makeup removal property equivalent to, or even greater than, that of the comparative compositions based on sodium lauryl sulphate.

Experiment 2

The detail of the tests carried out and the results are presented in Table 9 hereinafter.

TABLE 9

Tests and results of Experiment 2

| Test | Composition to be tested | % of makeup removed |
|---|---|---|
| Test 6 | 1 g of composition 3 according to the invention in 49 g of water | 90.99 |
| Test 7 | 5 g of composition 3 according to the invention in 49 g of water | 97.69 |
| Test 8 (control) | Water alone | 70.76 |

It can be seen that the proportion of makeup that was removed from the cap and transferred to the mixture of water/composition 3 according to the invention (tests 6 and 7) is appreciably greater than that removed from the caps and transferred into water alone (test 8).

EXAMPLE 7: REPLACING COCAMIDE DIETHANOLAMINE (COCAMIDE DEA) AND/OR SODIUM LAURYL ETHER SULPHATE (SLES) BY A CONCENTRATE ACCORDING TO THE INVENTION

Concentrate 7 according to the invention was used in the preparation of cleaning compositions of the detergent type for dishwashing or shampoo, by replacing cocamide DEA and/or SLES.

Cocamide DEA is a surfactant having good foaming and thickening properties.

The viscosity of the prepared compositions after one day was evaluated according to the method described in Example 2.

The volume of foam formed on the surface of the different compositions was evaluated according to the method described in Example 4.

The detail of the prepared cleaning compositions and the results of the different measurements are indicated in Table 10 hereinafter. The cleaning compositions are prepared by simple mixing of the components thereof.

TABLE 10

Prepared compositions and results of tests 9 to 16 of Example 7

| | Test 9 | Test 10 | Test 11 | Test 12 | Test 13 | Test 14 | Test 15 | Test 16 |
|---|---|---|---|---|---|---|---|---|
| | | | | %* | | | | |
| Euramid V (cocamide DEA) | 3 | | | | | | | |
| SLES (28% active) | 45 | 45 | 40 | 30 | 20 | 10 | 5 | 0 |
| Concentrate 7 according to the invention | 0 | 3 | 8 | 18 | 28 | 38 | 43 | 48 |

TABLE 10-continued

Prepared compositions and results of tests 9 to 16 of Example 7

|  | Test 9 | Test 10 | Test 11 | Test 12 | Test 13 | Test 14 | Test 15 | Test 16 |
|---|---|---|---|---|---|---|---|---|
|  |  |  |  | %* |  |  |  |  |
| Sodium benzoate | 0.5 | 0.5 | 0.5 | 0.5 | 0.5 | 0.5 | 0.5 | 0.5 |
| NaCl | 0 or 2 | 0 or 2 | 0 or 2 | 0 or 2 | 0 or 2 | 0 or 2 | 0 or 2 | 0 or 2 |
| Water | qsf 100 | qsf 100 | qsf 100 | qsf 100 | qsf 100 | qsf 100 | qsf 100 | qsf 100 |
| pH | 5-6 | 5-6 | 5-6 | 5-6 | 5-6 | 5-6 | 5-6 | 5-6 |
| Viscosity after 1 days (without NaCl) | 40 | 10 | 120 | 6100 | 7500 | 24500 | 29000 | 25000 |
| Viscosity after 1 days (with NaCl) | 6300 | 2020 | 1320 | 4100 | 8600 | 15200 | 17700 | 20900 |
| Appearance | clear | clear | clear | Foam, cloudy | Foam, cloudy | Foam, clear | Foam, cloudy | Foam, cloudy |
| Foam after 1 minute (with NaCl) | 850 | 760 | 780 | 770 | 800 | 900 | 780 | 850 |
| Foam after 10 minutes (with NaCl) | 860 | 760 | 780 | 770 | 800 | 880 | 760 | 830 |

*The percentages indicated are percentages by weight with respect to the total weight of the composition.

The results show that replacing SLES with increasing quantities of the concentrate according to the invention results in an increase in viscosity. This increase in viscosity is obtained despite the absence of cocamide DEA and NaCl.

Furthermore, the volume of foams formed on the surface of the different compositions is large.

A concentrate according to the invention is therefore a good solution for replacing cocamide DEA, sodium lauryl ether sulphate and/or sodium lauryl sulphate.

More particularly, a detergent composition prepared from a concentrate according to the invention will have both a high viscosity and a good foaming property.

Concentrates 15 and 17 according to the invention were also used in the preparation of cleaning compositions of the detergent type for dishwashing or shampoo, by replacing cocamide DEA and/or SLES (tests 17 and 18 respectively).

The pH of these compositions was adjusted to 5.8 by adding citric acid.

The viscosity of the prepared compositions after one day was evaluated according to the method described in Example 2.

The volume of foam formed on the surface of the different compositions was evaluated according to the method described in Example 4.

The detail of the cleaning compositions prepared and the results of the different measurements are indicated in Table 11 hereinafter. The cleaning compositions are prepared by simple mixing of the components thereof.

TABLE 11

Prepared compositions and results of tests 17 and 18 of Example 7

|  | Test 17 | Test 18 |
|---|---|---|
|  | %* |  |
| Euramid V (cocamide DEA) | 3 | 3 |
| SLES (28% active) | 20 | 20 |
| Concentrate 15 according to the invention | 28 |  |
| Concentrate 17 according to the invention |  | 28 |
| Sodium benzoate | 0.5 | 0.5 |
| NaCl | 0 | 0 |
| Water | qsf 100 | qsf 100 |
| pH | 5.8 | 5.8 |

TABLE 11-continued

Prepared compositions and results of tests 17 and 18 of Example 7

|  | Test 17 | Test 18 |
|---|---|---|
|  | %* |  |
| Viscosity after 1 day (without NaCl) | 7230 | 9032 |
| Appearance | cloudy | cloudy |
| Foam after 10 minutes | 770 | 820 |

*The percentages indicated are percentages by weight with respect to the total weight of the composition.

Again, the results show that the concentrates according to the invention are a good solution for replacing SLES.

In comparison with test 13 using concentrate 7, tests 17 and 18 show that concentrates 15 and 17 also allow an increase in viscosity, in particular in the absence of NaCl.

Furthermore, the volume of the foams formed on the surface of the different compositions is large.

A cleaning composition, such as a shampoo, prepared from a concentrate according to the invention will have both a high viscosity and a good foaming property.

The invention claimed is:

1. A concentrate comprising:
   20% to 70% by weight of at least one mannosylerythritol lipid (MEL), with respect to the total weight of the concentrate, and
   at least one polyglycerol fatty acid ester selected from the group consisting of polyglycerol-6 isostearate, polyglycerol-10 isostearate, polyglycerol-10 diisostearate, polyglycerol-6 laurate, polyglycerol-6 myristate, polyglycerol-6 stearate, polyglycerol-6 oleate, polyglycerol-10 oleate, polyglycerol-10 caprylate, polyglycerol-6 caprylate, polyglycerol-4 caprate, polyglycerol-4 laurate, polyglycerol-10 laurate, and combinations thereof,
   wherein a weight ratio mannosylerythritol lipid(s)/polyglycerol fatty acid ester(s) ranges from 1/3 to 2/1, and
   wherein a foam formed from an aqueous solution comprising said concentrate does not change its volume by more than 10% in 10 minutes from formation of the foam.

2. The concentrate according to claim 1, wherein the the weight ratio mannosylerythritol lipid(s)/polyglycerol fatty acid ester(s) ranges from 1/2 to 2/1.

3. The concentrate according to claim 1, comprising at least two MELs selected from the group consisting of MELs-A, MELs-B, MELs-C and MELs-D.

4. The concentrate according to claim 1, further comprising at least one glycerol fatty acid ester.

5. The concentrate according to claim 4, wherein the at least one glycerol fatty acid ester is a glycerol caprylic acid ester.

6. A composition comprising:
at least one MEL,
at least one polyglycerol fatty acid ester selected from the group consisting of polyglycerol-6 isostearate, polyglycerol-10 isostearate, polyglycerol-10 diisostearate, polyglycerol-6 laurate, polyglycerol-6 myristate, polyglycerol-6 stearate, polyglycerol-6 oleate, polyglycerol-10 oleate, polyglycerol-10 caprylate, polyglycerol-6 caprylate, polyglycerol-4 caprate, polyglycerol-4 laurate, polyglycerol-10 laurate, and combinations thereof, and
water,
wherein a weight ratio mannosylerythritol lipid(s)/polyglycerol fatty acid ester(s) is from 1/3 to 2/1, and
wherein a total quantity of MEL(s) and polyglycerol fatty acid ester(s) is from 3% and 75% by weight of the total weight of the composition.

7. A composition in a form of a solution, comprising:
at least one MEL,
at least one polyglycerol fatty acid ester selected from the group consisting of polyglycerol-6 isostearate, polyglycerol-10 isostearate, polyglycerol-10 diisostearate, polyglycerol-6 laurate, polyglycerol-6 myristate, polyglycerol-6 stearate, polyglycerol-6 oleate, polyglycerol-10 oleate, polyglycerol-10 caprylate, polyglycerol-6 caprylate, polyglycerol-4 caprate, polyglycerol-4 laurate, polyglycerol-10 laurate, and combinations thereof, and
water,
wherein a weight ratio mannosylerythritol lipid(s)/polyglycerol fatty acid ester(s) is from 1/3 to 2/1, and
wherein a total quantity of MEL(s) and polyglycerol fatty acid ester(s) expressed as a percentage by weight of the total weight of the composition is from 0.05 to less than 3.

8. A thickening agent, foaming agent and/or cleaning agent comprising the concentrate according to claim 1.

9. A method for cleaning a hard surface, dish, or human comprising applying to the hard surface, dish, or human the composition according to claim 6 with water.

10. A method for partially or totally replacing a surfactant in a shampoo or dishwashing detergent, comprising partially or totally replacing the surfactant with the concentrate according to claim 1, wherein the surfactant is selected from the group consisting of sodium lauryl sulphate, sodium lauryl ether sulphate, cocamide diethanolamine, and combinations thereof.

11. A shampoo or dishwashing detergent comprising the concentrate of claim 1.

12. A method of thickening water comprising adding the concentrate of claim 1 to water.

* * * * *